United States Patent [19]

Lovelock

[11] 4,025,794
[45] May 24, 1977

[54] IONIZATION DETECTORS WITH IRON-55 AS A RADIOACTIVE SOURCE

[76] Inventor: James Ephraim Lovelock, Bowerchalke, Salisbury, Wiltshire, England

[22] Filed: Oct. 20, 1975

[21] Appl. No.: 624,196

[30] Foreign Application Priority Data

Oct. 22, 1974 United Kingdom ............ 45758/74

[52] U.S. Cl. ............................... 250/381; 250/384
[51] Int. Cl.² ......................................... G01T 1/18
[58] Field of Search .......... 250/304, 306, 308, 381, 250/384, 375; 313/54, 93

[56] References Cited

UNITED STATES PATENTS

| | | | |
|---|---|---|---|
| 3,144,559 | 8/1964 | Forrester et al. | 250/384 |
| 3,560,737 | 2/1971 | Skildum | 250/384 |
| 3,566,107 | 2/1971 | Taylor et al. | 250/381 |
| 3,601,609 | 8/1971 | Yauger, Jr. | 250/375 |
| 3,714,421 | 1/1973 | Josias et al. | 250/381 |

*Primary Examiner*—Davis L. Willis
*Attorney, Agent, or Firm*—Woodhams, Blanchard and Flynn

[57] ABSTRACT

Ionization detector capable of operation at elevated temperatures and utilizing iron-55 as a radioactive source within the ionization chamber.

3 Claims, 2 Drawing Figures

-FIG.1-

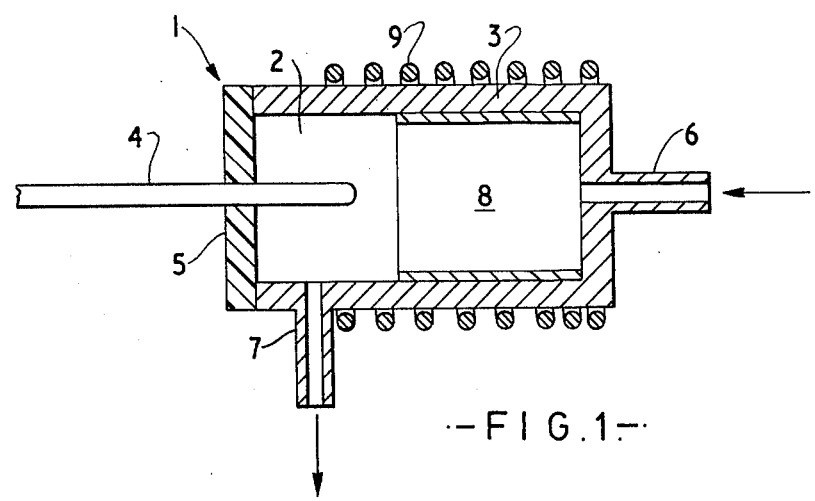
-FIG.1.-
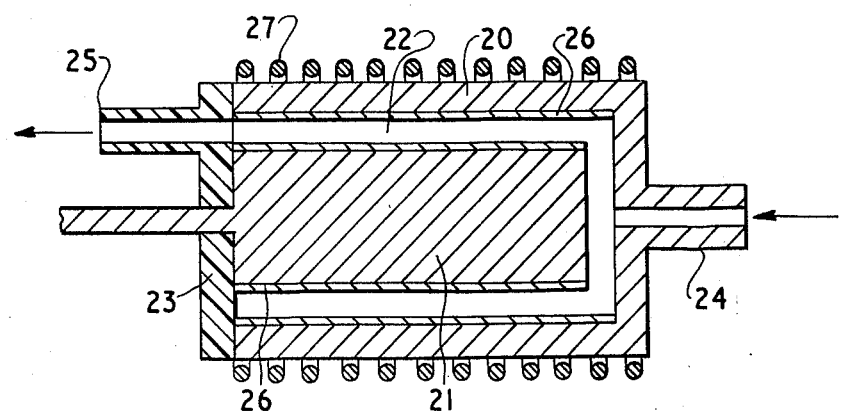
-FIG.2.-

IONIZATION DETECTORS WITH IRON-55 AS A RADIOACTIVE SOURCE

The present invention concerns ionization detectors.

Ionization detectors can be arranged and adapted to function in a number of modes, for example, as electron capture detectors, ionization cross-section detectors and argon ionization detectors.

Basically an ionization detector comprises a simple diode having inlet and outlet gas flow ports and containing a source of ionizing radiation to ionise a gas flowing through the detector. Tritium and nickel-63 are examples of radioactive sources employed in the detectors.

When used as an electro capture detector a carrier gas, such as nitrogen, on flowing through the ionization chamber is ionized by emission from the source resulting in the formation of free electrons. If a trace of a material containing molecules which are electron absorbing is introduced into the carrier gas flow some of the free electrons will be captured by these molecules. The reduction in the number of free electrons can be revealed by a decrease in standing current when a constant low potential is applied across the ionization chamber or by a pulse sampling method in which the electrodes are strongly polarised by a succession of short pulses at relatively long intervals. However both methods of operation suffer the disadvantage of a non-linear relationship between the detector current and the concentration of electron capture material introduced into the detector.

This disadvantage of non-linearity can be avoided by a pulse feedback method of operation in which the frequency of a pulse generator supplying pulses to the detector is adjusted in response to an electrometer output signal. Such an arrangement is disclosed in British patent specification No. 1,239,209. However in certain applications a desirable linear response can only be achieved upon penalty of a considerable loss in detectivity. By detectivity is meant signal to noise ratio and clearly this ratio must be as large as possible for practical purposes.

The present invention seeks to provide an ionization detector having a wide linear range and without penalty of a loss of detectivity.

This can be achieved by utilising as a source of ionizing radiation a material which produces a reduced number of ion pairs within the ionization chamber for each ionizing radiation particle emitted by the source.

Thus according to the present invention there is provided an ionization detector comprising an ionization chamber having inlet and outlet means for directing a gas flow through the chamber and an iron-55 radioactive source within the chamber to emit ionizing radiation into the gas flow.

Both tritium and nickel-63 produce a large number of ion pairs for each emitted ionizing particle. In ionization detectors it is accepted that the noise level is related to the square root of the number of ionizing events in unit time withing the ionization chamber. Therefore to produce a given ion current and a minimum noise level it is desirable to employ a radioactive source which produces the smallest number of ion pairs for each ionizing event. Generally a high ionization current in the region of 10 nano amps, i.e. $10^{-8}$ amp, is sought in an electron capture detector. However the linearity of the response when utilising the pulse feedback method can be improved if the ionization current is kept at a low level. While the current level can be reduced by reducing the size of the source in the case of conventional sources, such as tritium and nickel-63, by virtue of the use of iron-55 it is possible to retain the maximum possible physical size of radioactive source and yet produce a reduced number of ion pairs for each ionizing event.

Other considerations to be borne in mind in selecting a detector source are operating temperatures, cost and availability. Tritium is not recommended for use at elevated temperatures, for example, temperatures in excess of 200° C, as at such high temperatures tritum tends to leak into the atmosphere thereby creating an operating hazard. Iron-55 however is stable at the highest temperatures likely to be encountered during use of the detector in gas chromatography. Iron-55 sources upon heating to 400° C for extended periods showed no deterioration or damage when later checked at ambient temperature. The sources are further stable towards moisture. Iron-55 has a half-life of 2.6 years, a more than adequate half-life for ionization detectors. Finally, iron-55 is readily available and can be applied as by plating to a support surface.

The invention will be described further, by way of example, with reference to the accompanying drawings; in which:

FIG. 1 is a diagrammatic longitudinal cross-section of an ionization detector having an Iron-55 radioactive source; and FIG. 2 is a diagrammatic longitudinal cross-section of an alternative form of ionization detector having an Iron-55 radioactive source.

In FIG. 1, an ionization detector, which can function for example an an electron capture detector, comprises a hollow cylindrical body 1 defining an ionization chamber 2. The cylindrical wall 3 of the chamber defines a first electrode. The second electrode 4 can be an elongate wire or rod coaxially arranged within the chamber 2 and supported by a bush 5 of electrically insulating material. The chamber is provided with an inlet 6 and an outlet 7 for a gas flow. The chamber contains a radioactive source 8 of Iron-55. In FIG. 1 the source 8 is shown deposited on the wall of the chamber. However the source can be deposited on to the inner electrode 4 or on to both the outer and inner electrodes. The source can be deposited on the electrodes by electro-plating. Alternatively the source can be deposited on a separate foil or carrier which is then located in the ionization chamber. For example, the separate carrier can comprise a cylindrical metal foil which is dimensioned to fit within the chamber 2. The detector can be raised to elevated temperatures by means of a heating coil 9 about its exterior. Alternatively, a cartridge heater can be located in a wall of the chamber or a heating current can be passed directly through the wall of the chamber.

In FIG. 2, the detector comprises a hollow outer electrode 20 and an inner cylindrical electrode 21 which is supported within and spaced from the outer electrode to define an annular chamber 22 therebetween. The inner electrode 21 can be supported by an end plate or disc 23 of electrically insulating material. A gas inlet 24 and a gas outlet 25 convey gas into and out of the annular chamber 22. An Iron-55 radio-active source 26 is deposited upon one or both walls defining the annular chamber. In FIG. 2 the source is shown deposited both upon the inner electrode and the outer electrode. The detector can be heated to elevated temperatures ad by a heating coil 27.

Both the detectors of FIGS. 1 and 2 can be operated by a direct current supply or by a pulsed polarising voltage. The operating conditions and electrode spacing will be determined by the mode of operation of the detector as is known in the art. In addition other detector geometries and configurations are possible.

A radioactive source of Iron-55 was compared with sources of tritium and nickel-63. In each case the detector was a simple diode ion-chamber having a diameter of 1.25cm., a length of 1.25 cm. and a coaxial anode 1 mm. in diameter. The comparisons were made at a temperature of 21°C, ambient pressure, and nitrogen carrier gas flowing at a rate of 1 ml./second.

The results are listed in the table. Minimum noise is obtained with iron-55. The activity of one of the nickel-63 sources was chosed to provide substantially the same saturation current as that given by the iron-55 source. The results indicate that the strength of the iron-55 source is required to be about ten times that of the nickel-63 source to attain the given ion current while the associated noise level is greater with the nickel-63 source.

Signal strengths were also recorded upon introducing Freon-11 and carbon tetrachloride into the carrier gas flow, the detector operating as an electron capture detector. The concentration of Freon-11 and carbon tetrachloride was the same for each detector and source. The signal strengths are given in the table together with the signal to noise ratio.

The results demonstrate that iron-55 provides a high signal to noise ratio at a considerably lower ion current than is usually employed in gas chromatography. The iron-55 is stable and convenient to apply as a radiation source.

TABLE

A COMPARISON OF IONIZING SOURCES

| Source | mCi | $I_o$ p.amps × 10$^3$ | $I_{op}$ | Noise p.amps | Signal p.amps F-11 | CCl$_4$ | Signal/Noise ratio F-11 | CCl$_4$ |
|---|---|---|---|---|---|---|---|---|
| Tritium | 500 | 30 | 15 | 3 | 132 | 30 | 44 | 10 |
| Ni-63 | 15 | 9 | 5.3 | 1.5 | 80 | 19 | 54 | 13 |
| Ni-63 | 0.5 | 0.48 | 0.34 | 0.4 | 10 | 2.8 | 25 | 7 |
| Fe-55 | 5 | 0.5 | 0.3 | 0.1 | 6.4 | 1.7 | 64 | 17 |

$I_o$ - DC saturation current
$I_{op}$ - operating current

I claim:

1. An ionization detector comprising an ionization chamber, inlet and outlet means for directing gas through the chamber, electrode means within the chamber in ionization detection relationship and an iron-55 radioactive source within the chamber to emit ionizing radiation particles into the gaseous matter.

2. An ionization detector according to claim 1 in which the iron-55 source is plated on to at least one electrode.

3. An ionization detector according to claim 1 including heating means for maintaining the chamber at elevated temperatures.

* * * * *